(12) United States Patent
Miller et al.

(10) Patent No.: US 6,786,886 B2
(45) Date of Patent: Sep. 7, 2004

(54) METHOD FOR STABILIZING BALLOON DURING DILATION

(75) Inventors: Paul J. Miller, St. Paul, MN (US); Matthew J. Tracy, St. Michael, MN (US)

(73) Assignee: SciMed Life Systems, Inc., Maple Grove, MN (US)

( * ) Notice: Subject to any disclaimer, the term of this patent is extended or adjusted under 35 U.S.C. 154(b) by 0 days.

(21) Appl. No.: 09/682,198

(22) Filed: Aug. 3, 2001

(65) Prior Publication Data

US 2003/0028234 A1 Feb. 6, 2003

(51) Int. Cl.⁷ .............................................. A61M 29/00
(52) U.S. Cl. ............................ 604/96.01; 604/103.04
(58) Field of Search .................... 640/96.01, 98.01, 640/99.02, 99.04, 103.04, 915–921, 101.02, 920, 97.01, 192

(56) References Cited

U.S. PATENT DOCUMENTS

| | | | |
|---|---|---|---|
| 4,820,349 A | 4/1989 | Saab | 128/344 |
| 4,932,959 A * | 6/1990 | Horzewski et al. | 606/194 |
| 4,936,310 A | 6/1990 | Engstrom et al. | 128/673 |
| 5,085,636 A | 2/1992 | Burns | 604/99 |
| 5,217,434 A | 6/1993 | Arney | 604/99 |
| 5,221,260 A * | 6/1993 | Burns et al. | 604/913 |
| 5,324,259 A * | 6/1994 | Taylor et al. | 604/99.04 |
| 5,531,689 A | 7/1996 | Burns et al. | 604/99 |
| 5,628,754 A | 5/1997 | Shevlin et al. | 606/108 |
| 5,738,901 A | 4/1998 | Wang et al. | 427/2.3 |
| 5,826,588 A | 10/1998 | Forman | 128/898 |
| 5,843,032 A | 12/1998 | Kastenhofer | 604/96 |
| 5,876,376 A * | 3/1999 | Schwab et al. | 604/103 |
| 5,919,162 A | 7/1999 | Burns | 604/99 |
| 6,066,157 A | 5/2000 | Barbere | 606/194 |
| 6,096,009 A * | 8/2000 | Windheuser et al. | 604/165.01 |
| 6,096,525 A | 8/2000 | Patnaik | 435/181 |
| 6,097,976 A | 8/2000 | Yang et al. | 600/373 |
| 6,117,140 A | 9/2000 | Munsinger | 606/108 |
| 6,120,522 A * | 9/2000 | Vrba et al. | 606/190 |
| 6,129,707 A * | 10/2000 | Cryer | 604/96.01 |
| 6,168,748 B1 | 1/2001 | Wang et al. | 264/520 |
| 6,193,738 B1 | 2/2001 | Tomaschko et al. | 606/194 |
| 6,231,543 B1 | 5/2001 | Hegde et al. | 604/96.01 |

FOREIGN PATENT DOCUMENTS

EP   0 371 486   9/1990

* cited by examiner

*Primary Examiner*—Brian L. Casler
*Assistant Examiner*—Lina R Kontos
(74) *Attorney, Agent, or Firm*—Vidas, Arrett & Steinkraus

(57) ABSTRACT

A balloon catheter comprises an inner tube, a medical balloon and an inflation lumen. The medical balloon is disposed about the inner tube and in fluid communication with the inflation lumen. A collapsible portion of the inner tube is constructed to collapse inward upon delivery of an inflation fluid to the medical balloon to secure the inner tube to the guidewire.

14 Claims, 9 Drawing Sheets

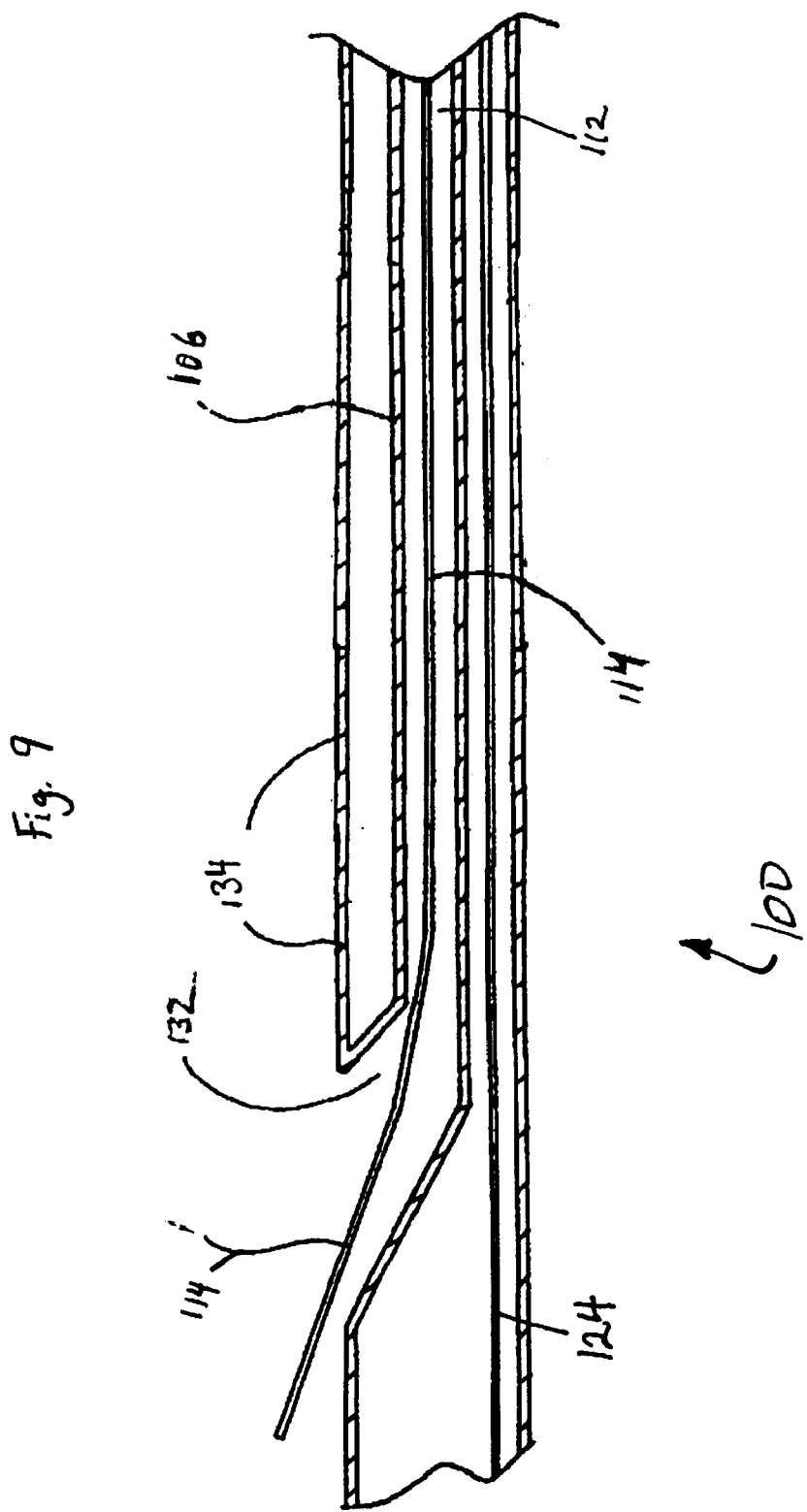

METHOD FOR STABILIZING BALLOON DURING DILATION

BACKGROUND OF INVENTION

Medical balloons have been used in a number of different applications including dilation of bodily vessels and expansion of medical devices such as stents. In the former application, the medical balloon is delivered on a catheter to a stricture in a vessel and expanded to open the stricture. Expansion of the balloon compresses any plaque present at the stricture. In the latter application, a stent, stent-graft, graft or other prosthesis disposed about a medical balloon may be delivered on a catheter to a desired location in a bodily vessel and expanded by inflating the balloon.

In delivering the medical balloon to the desired bodily location, the catheter must traverse tortuous bodily vessels. Typically, a guidewire will be used to facilitate delivery of the catheter to the desired bodily location. In the case of an over-the-wire (OTW) catheter, for example, the guidewire is positioned within a lumen of an over-the-wire catheter with the distal tip of the guidewire just proximal to the distal tip of the catheter. The catheter and guidewire are advanced through a guiding catheter to the distal end thereof. The guidewire is then advanced out of the distal end of the guiding catheter into the patient's coronary vasculature until the distal end of the guidewire crosses the desired location in the vessel. The catheter is next advanced out of the guiding catheter until the catheter balloon is properly positioned.

To facilitate delivery of the balloon, it has proven advantageous to apply lubricious coatings to various portions of the medical balloon and other components of the catheter including the various tubes that form the catheter.

Although the use of lubricious coatings has proven beneficial, the presence of such coatings may, in certain cases, result in "watermelon seeding". Where a highly lubricious balloon and a highly lubricious outer shaft is used, the balloon may slip from the constraints of the lesion as the balloon is inflated. "Watermelon seeding", as the slippage is known, can result in inaccurate vessel dilation or inaccurate placement of the stent or other prosthesis. To avoid this, the balloon must be repositioned, adding to the time required by the procedure.

Where the balloon remains fixed in place, another problem which may be encountered involves sliding of a guidewire relative to the balloon.

There remains a need for inventive catheter designs which are not plagued by the problem of "watermelon seeding" and for inventive catheters which do not experience slippage of the guidewire. More generally, there remains a need for inventive balloon catheters which do not experience undesired motion upon inflation of the balloon.

All US patents and applications all other published documents mentioned anywhere in this application are incorporated herein by reference in their entirety.

Without limiting the scope of the invention, a brief summary of the claimed embodiments of the invention is set forth below. Additional details of the summarized embodiments of the invention and/or additional embodiments of the invention may be found in the Detailed Description of the Invention below.

A brief abstract of the technical disclosure in the specification is provided as well for the purposes of complying with 37 C.F.R. 1.72.

SUMMARY OF INVENTION

The invention is directed in one aspect to a balloon catheter comprising an inner tube with a guidewire therein, a medical balloon and an inflation lumen. The medical balloon is disposed about the inner tube and in fluid communication with the inflation lumen. A collapsible portion of the inner tube is constructed to collapse inward upon delivery of an inflation fluid to the medical balloon and grip the guidewire and to release the guidewire upon removal of the inflation fluid. Desirably, the collapsible portion of the inner tube is a distal portion of the inner tube.

In one embodiment of the invention, the collapsible portion of the inner tube is made of an elastomeric material. Desirably, portions of the inner tube adjacent the elastomeric material are made of a non-elastomeric material. In another embodiment, the collapsible portion is at least 2 mm long.

In another embodiment of the invention, the inner tube is characterized by a plurality of wall thicknesses and the wall thickness of at least a portion of the collapsible portion of the inner tube is smaller than the wall thickness of portions of the inner tube adjacent the collapsible portion. Desirably, the wall thickness of the collapsible portion is 0.002 inches or less. The portions of reduced wall thickness may be in the form of circumferential bands, bands which extend about only a portion of the circumference of the inner tube and/or slots which may desirably be substantially longitudinal.

Also, the inner tubes of the inventive balloon catheters may be provided with a plurality of collapsible portions.

The invention is also directed to a balloon catheter comprising an inner tube with a guidewire therein, a medical balloon and an inflation lumen. The medical balloon is disposed about the inner tube and in fluid communication with the inflation lumen. The inner tube includes a first portion and a second portion adjacent the first portion. The second portion is weaker than the first portion and deforms inward upon delivery of an inflation fluid to the medical balloon. The inner tube may optionally comprise a plurality of weaker portions. Locking occurs for inflation beyond a few atmospheres. Desirably, the second portion recoils upon the removal of inflation fluid from the balloon.

The inventive balloon catheter may be provided with a guidewire in the inner tube when manufactured, at the point of use or at any other suitable time. In use, when an inflation fluid is supplied to the medical balloon, the collapsible portion collapses inward on the guidewire securing the inner tube to the guidewire.

The invention is also directed to a balloon catheter comprising an inner tube with a guidewire therein, a medical balloon disposed about the inner tube and an inflation lumen in fluid communication with the medical balloon. A collapsible portion of the inner tube is constructed to collapse inward upon pressurizing the balloon to grip the guidewire and to release the guidewire upon depressurizing the balloon.

The inventive balloon catheters may optionally be provided with a prosthesis disposed about the medical balloon. Suitable prostheses include stents, stent-grafts and grafts.

The inventive balloon catheters may be provided in a number of different configurations including in a rapid exchange configuration, an over-the-wire configuration and a convertible configuration.

In another aspect, the invention is directed to a method of securing a catheter inner tube to a guidewire disposed in the inner tube comprising the steps of providing an inventive balloon catheter as disclosed herein, delivering an inflation fluid to the medical balloon to cause the collapsible portion of the inner tube to collapse inward against the guidewire and secure the inner tube to the guidewire. Upon removal of the inflation fluid from the medical balloon, the collapsible portion of the inner tube desirably releases the guidewire.

In another aspect, the invention is directed to a method of dilating a vessel comprising the steps of providing an inventive balloon catheter as disclosed herein, inserting the catheter in a body and delivering the medical balloon to a desired location in a bodily vessel and inflating the medical balloon to a pressure sufficient to apply a force to the vessel by supplying an inflation fluid to the medical balloon, the supplying of inflation fluid causing the collapsible portion of the inner tube to collapse inward against the guidewire and secure the inner tube to the guidewire. Upon deflation of the medical balloon, the collapsible portion of the inner tube desirably releases the guidewire.

In yet another aspect, the invention is directed to a method of delivering a prosthesis to a desired location in a bodily vessel comprising the steps of providing an inventive balloon catheter as disclosed herein with a prosthesis disposed about the medical balloon, inserting the catheter in a body and delivering the medical balloon to a desired location in a bodily vessel, and inflating the medical balloon to a pressure sufficient to expand the prosthesis and implant the prosthesis in the vessel by supplying an inflation fluid to the medical balloon, the supplying of inflation fluid causing the collapsible portion of the inner tube to collapse inward against the guidewire and secure the inner tube to the guidewire. Upon removal of the inflation fluid from the medical balloon, the collapsible portion of the inner tube desirably releases the guidewire.

Additional details and/or embodiments of the invention are discussed below.

BRIEF DESCRIPTION OF DRAWINGS

FIG. 9 shows a portion of a catheter in a rapid exchange configuration.

DETAILED DESCRIPTION

Figure 1:
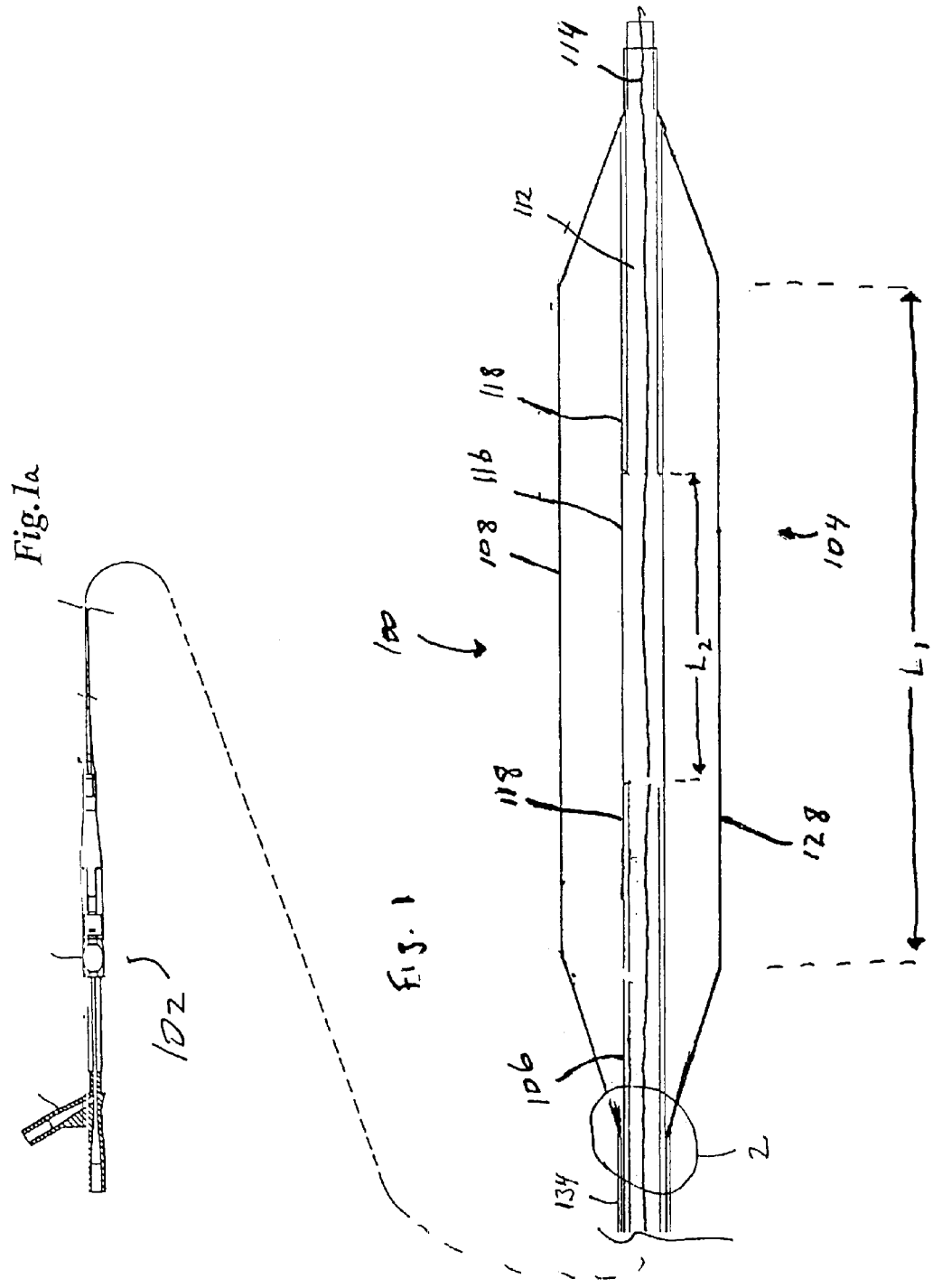
FIG. 1 is a side view of an inventive balloon catheter with parts cut away at the distal end, the inner tube including a collapsible portion made of a material different from adjacent portions of the inner tube.

While this invention may be embodied in many different forms, there are described in detail herein specific preferred embodiments of the invention. This description is an exemplification of the principles of the invention and is not intended to limit the invention to the particular embodiments illustrated.

For the purposes of this disclosure, like reference numerals in the figures shall refer to like features unless otherwise indicated.

Figure 2:
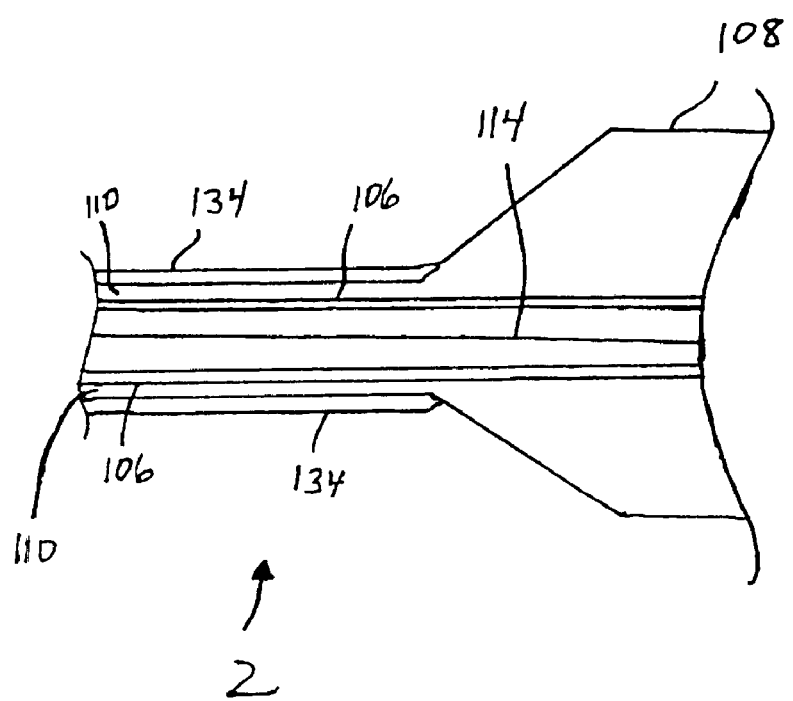
FIG. 2 is an enlarged view of portion 2 of FIG. 1.

In one embodiment, the instant invention is directed to a balloon catheter shown generally at 100 in FIG. 1. Balloon catheter 100 has a proximal end 102 with a manifold and a distal end 104 and comprises inner tube 106 and outer tube 134 disposed about inner tube 106. The catheter of FIG. 1 is shown with a change of scale between the proximal and distal ends. Inner tube 106 extends to distal end 104 of catheter 100. Medical balloon 108 is disposed about the distal end of inner tube 106. The space between outer tube 134 and inner tube 106, as shown in circled region 2 of FIG. 1 and as shown in greater detail in FIG. 2, defines inflation lumen 110 which is in fluid communication with medical balloon 108. Medical balloon 108 may be inflated by supplying an inflation fluid thereto via inflation lumen 110. Inner tube 108 has a lumen 112 extending therethrough through which optional guidewire 114 extends. Guidewire 114 may optionally be provided in inner tube 106 when the catheter is manufactured or may be disposed therein at the point of use.

Inner tube 106 includes a collapsible portion 116, desirably toward the distal end of the inner tube, which is constructed to collapse inward upon delivery of an inflation fluid to medical balloon 108. As shown in FIG. 1, collapsible portion 116 is made of a different material from those portions 118 of the inner tube adjacent to the collapsible portion. Desirably, the collapsible portion of the inner tube is made of an elastomeric material. Suitable elastomeric materials include PEBAX, polyurethane, silicone and thermoplastic elastomers. Also desirably, the portions 118 of inner tube 106 adjacent collapsible portion 116 are made of a non-elastomeric material. Suitable non-elastomeric materials include high density polyethylene, nylon and high durometer PEBAX. Collapsible portion 116 may be attached to the adjacent portions 118 of inner tube 106 via a suitable adhesive, by laser welding, heat welding or any other suitable technique. The particular joining technique will depend on the choice of materials for the inner tube and elastomeric portion and the available resources.

Desirably, the collapsible portion of the inner tube releases from its collapsed position upon removal of the inflation fluid from the medical balloon to release the guidewire. More desirably, the collapsible portion of the inner tube will recoil from its collapsed position upon removal of the inflation fluid from the medical balloon.

Figure 3:
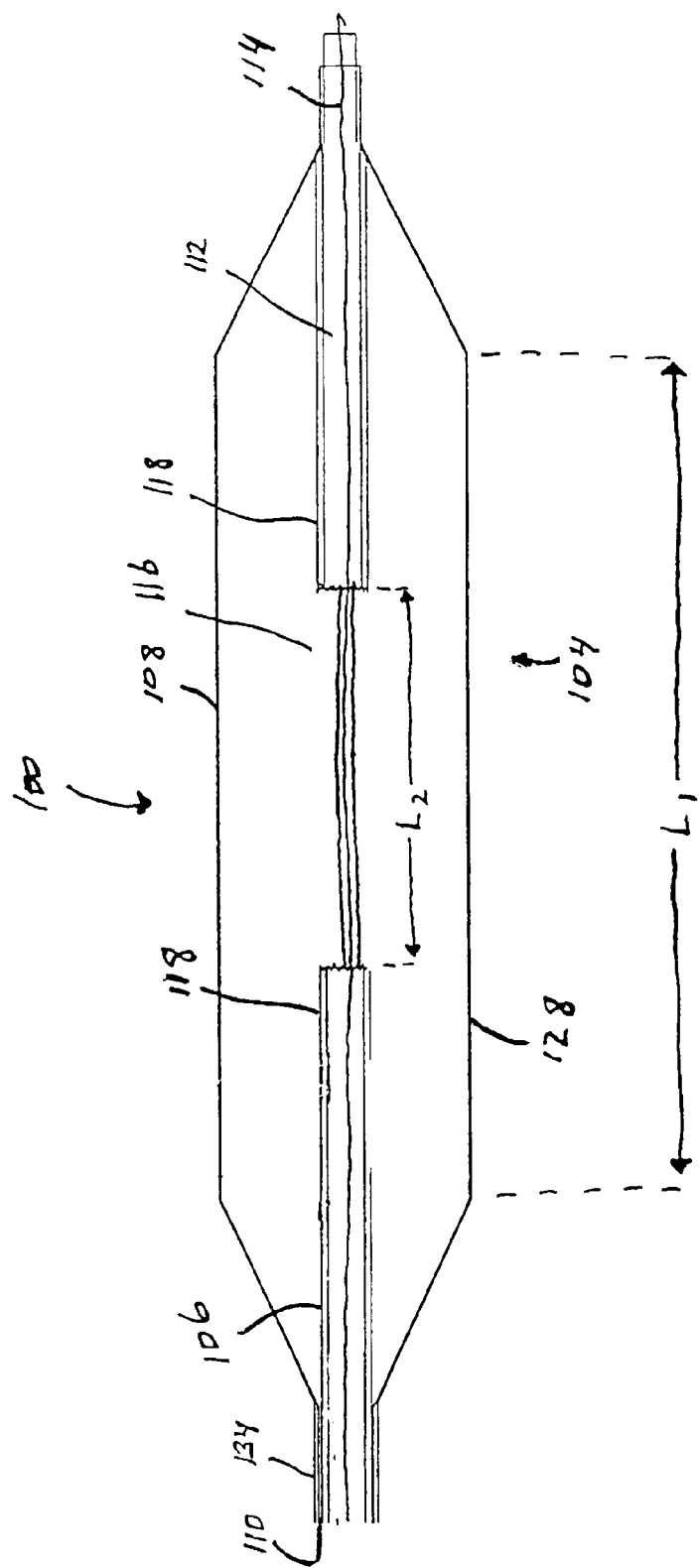
FIG. 3 is a side view of an the inventive balloon catheter of FIG. 1 with the balloon partially inflated and the collapsible portion partially collapsed inward.

The catheter of FIG. 1 is shown in FIG. 3 with the balloon at least partially inflated. The pressure of the inflation fluid has caused collapsible portion 116 to collapse part of the way inward. With the supplying of additional inflation fluid to the balloon, the collapsible portion would collapse further inward and temporarily secure inner tube 106 to guidewire 114.

Figure 4:
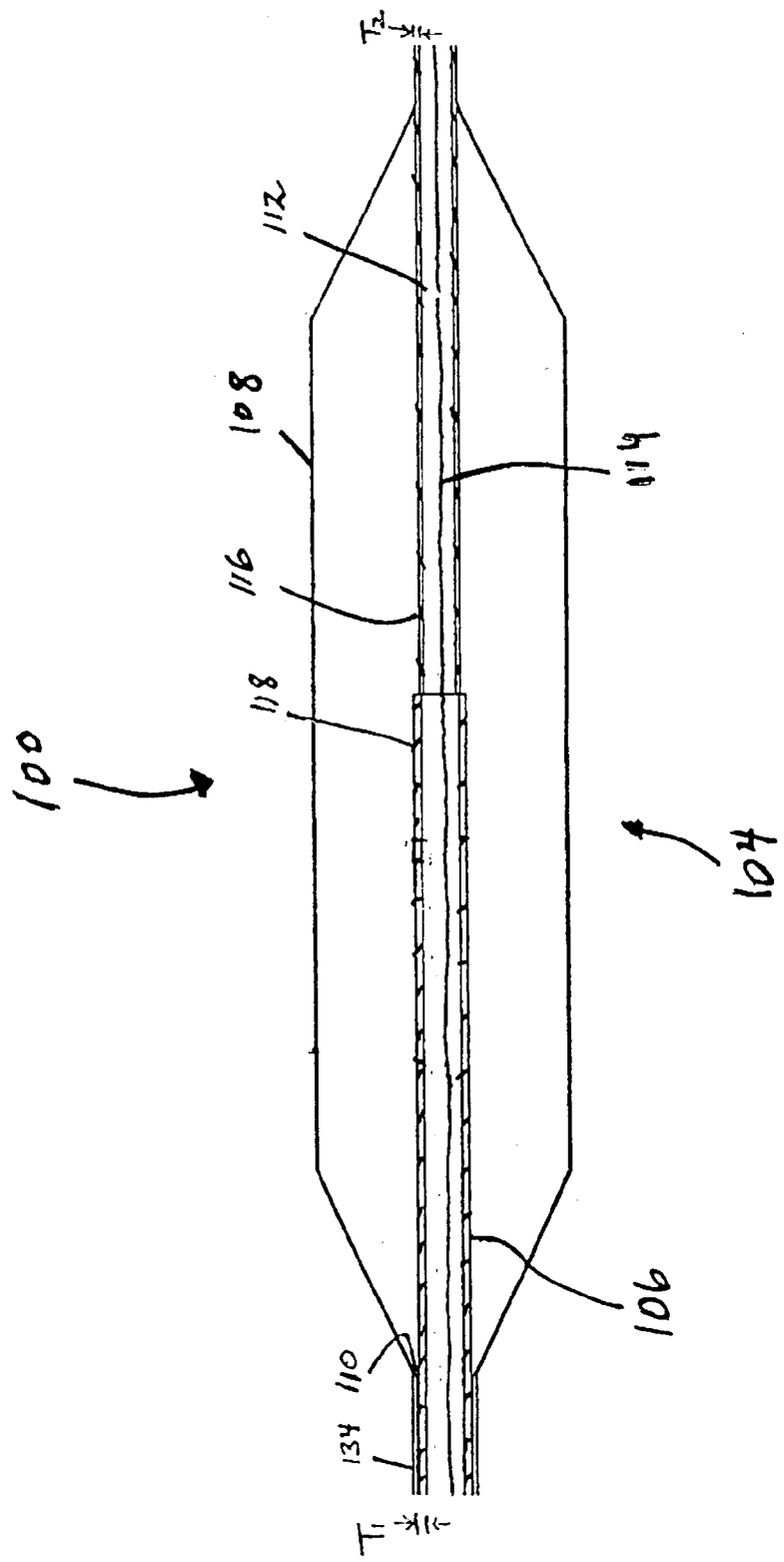
FIG. 4 is a side view of an inventive balloon catheter with parts cut away at the distal end, the inner tube including a collapsible portion of a thinner wall thickness than adjacent portions of the inner tube.

In another embodiment of the invention as shown generally at 100 in FIG. 4, at least a portion of collapsible portion 116 of inner tube 106 has a wall thickness $T_2$ which is smaller than the wall thickness $T_1$ of those portions 118 of inner tube 106 which are adjacent to collapsible portion 116. Collapsible portion 116 may be made of an elastomeric material as described above with respect to the embodiment of FIGS. 1–2 or a non-elastomeric material. In the latter case, the collapsible portion may be made of the same material as the remainder of the inner tube as long as the wall thickness $T_2$ is thinner than $T_1$ and the collapsible portion of the inner tube can collapse inward upon supplying an inflation fluid to the medical balloon. Desirably, the wall thickness of the collapsible portion is no more than 0.002 inches thick. The entirety of the wall of the collapsible portion may be of reduced wall thickness or only a portion of the wall of the collapsible portion may be of reduced wall thickness. Also desirably, the collapsible portions will be of a smaller diameter than portions of the inner tube which are adjacent to the collapsible portions. As with the previous embodiment, the collapsible portion is constructed to collapse inward on the guidewire to secure the inner tube to the guidewire and desirably, to release the guidewire upon removal of the inflation fluid from the medical balloon. More desirably, the collapsible portion recoils upon removal of the inflation fluid.

Figure 5:
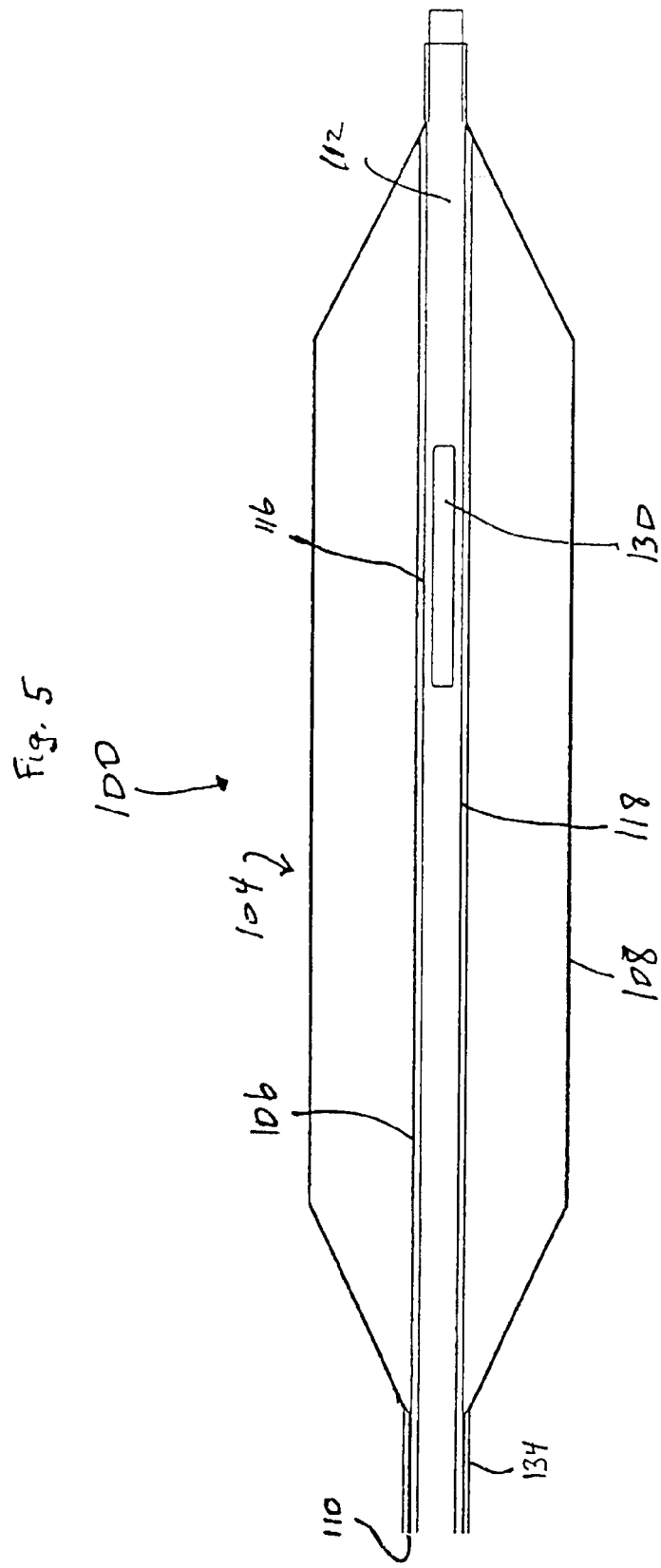
FIG. 5 is a side view of an inventive balloon catheter with parts cut away at the distal end, the inner tube comprising a plurality of slots in the distal portion.

An example of an embodiment in which only a portion of the collapsible portion is of reduced wall thickness is shown generally at 100 in FIG. 5. In the embodiment of FIG. 5, collapsible portion 116 of inner tube 106 has at least one slot 130 therein. The wall thickness of the collapsible portion in the region of the slots is thinner than the wall thickness of the remainder of the collapsible portion of the inner tube.

Slot 130, as shown in FIG. 5, has a rectangular configuration. The invention contemplates other slot configurations as well. For example, the slot could be helical or in the form of bands which extend at least partially and desirably about the entirety of the circumference of the inner tube. More generally, slots may be provided with any other desirable shape.

Figure 6:
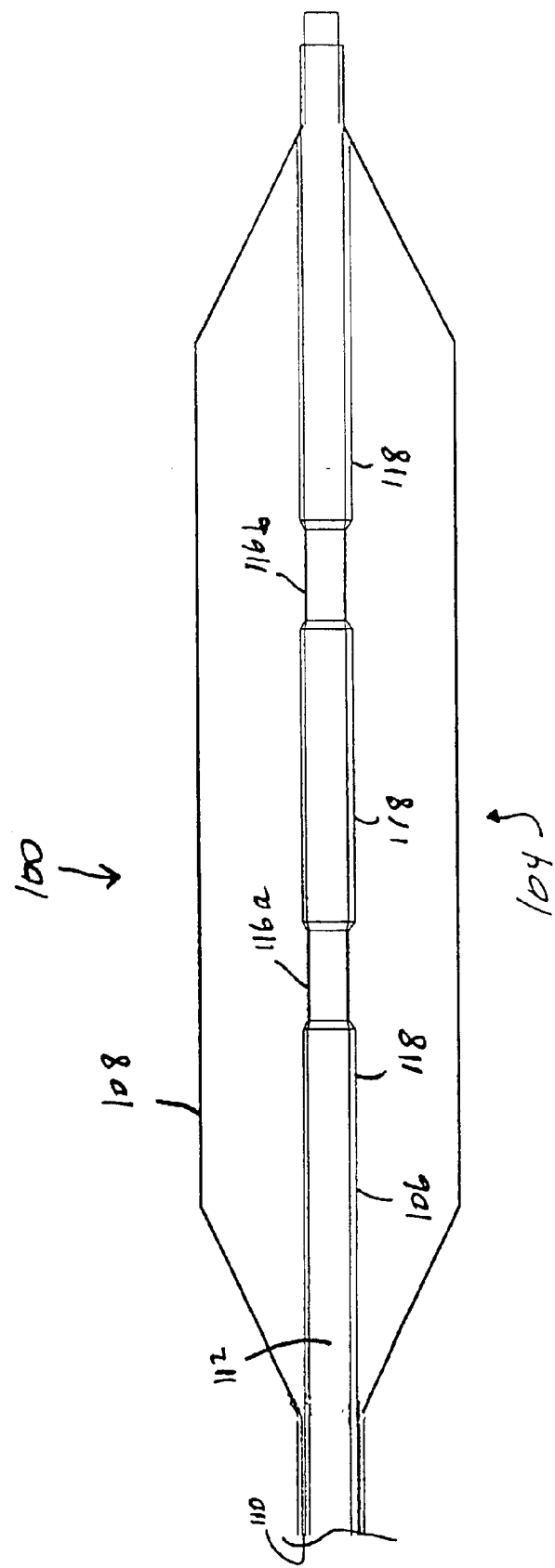
FIG. 6 is a side view of an inventive balloon catheter similar to that of FIG. 4 with a plurality of collapsible portions.

In any of the embodiments described above and below, the inner tube may comprise a plurality of collapsible portions. As shown in FIG. 6, inner tube 106 of catheter 100 comprises two collapsible portions 116a and 116b both of which have thinner wall thicknesses than adjacent portions 118 of inner tube 106. Other embodiments of the invention may have three, four, five, six, seven, eight or more collapsible portions.

More generally, the collapsible portion of the inner tube may be a portion of the inner tube which is weakened relative to adjacent portions of the inner tube. The weakening may result from the collapsible portion have a reduced wall thickness relative to adjacent portions of the inner tube. A reduced wall thickness may be achieved by removing material from the wall in the collapsible portion using mechanical techniques such as grinding, using laser ablation techniques, etching techniques or bonding a thinner walled tube to the end of a thicker walled tube. Suitable materials removal techniques are disclosed in copending U.S. application Ser. No. 09/401,618 as well as in U.S. Pat. No. 5,826,588. A single region of reduced wall thickness may be provided or a plurality of separate regions of reduced wall thickness may be provided. Slots may be provided in the weaker portion or the material may be dimpled or otherwise weakened.

The weakening may also result from the collapsible portion being differently treated from adjacent portions of the inner tube. For example, the collapsible portion may be differently heat treated or differently treated chemically to weaken the collapsible portion.

Where the inner tube comprises a plurality of layers, as disclosed for example in U.S. Pat. No. 5,843,032, one or more outer layers of the inner tube may be removed by any suitable technique including grinding, etching and laser ablation. The inner tube disclosed in U.S. Pat. No. 5,843,032 may optionally include a polyethylene (desirably high density) inner layer and a polyamide outer layer, a portion of which may be removed. A trilayer tube suitable for use may optionally have an outer layer of PEBAX, an inner layer of polyethylene (desirably high density) and an intermediate layer of Plexar. A portion of the outer and, optionally, intermediate layer may be removed.

The weakening may also result from the tube having a portion which comprises a weaker or more flexible material.

The invention is also directed to a balloon catheter comprising an inner tube, a medical balloon and an inflation lumen. The medical balloon is disposed about the inner tube and in fluid communication with the inflation lumen. The inner tube includes a first portion and a second portion adjacent the first portion. The second portion is weaker than the first portion and deforms inward upon delivery of an inflation fluid to the medical balloon. The inner tube may optionally comprise a plurality of weaker portions. The weaker portion(s) may be formed using any of the techniques described above or below.

The catheter may be provided for the purposes of angioplasty. With this application in mind, suitable angioplasty balloons will be used. Examples of suitable balloon materials for use in angioplasty balloons are disclosed in U.S. Pat. No. 6,168,748 and U.S. Pat. No. 5,738,901. The shape and construction of the balloon may be that of any known angioplasty balloon.

Figure 7:
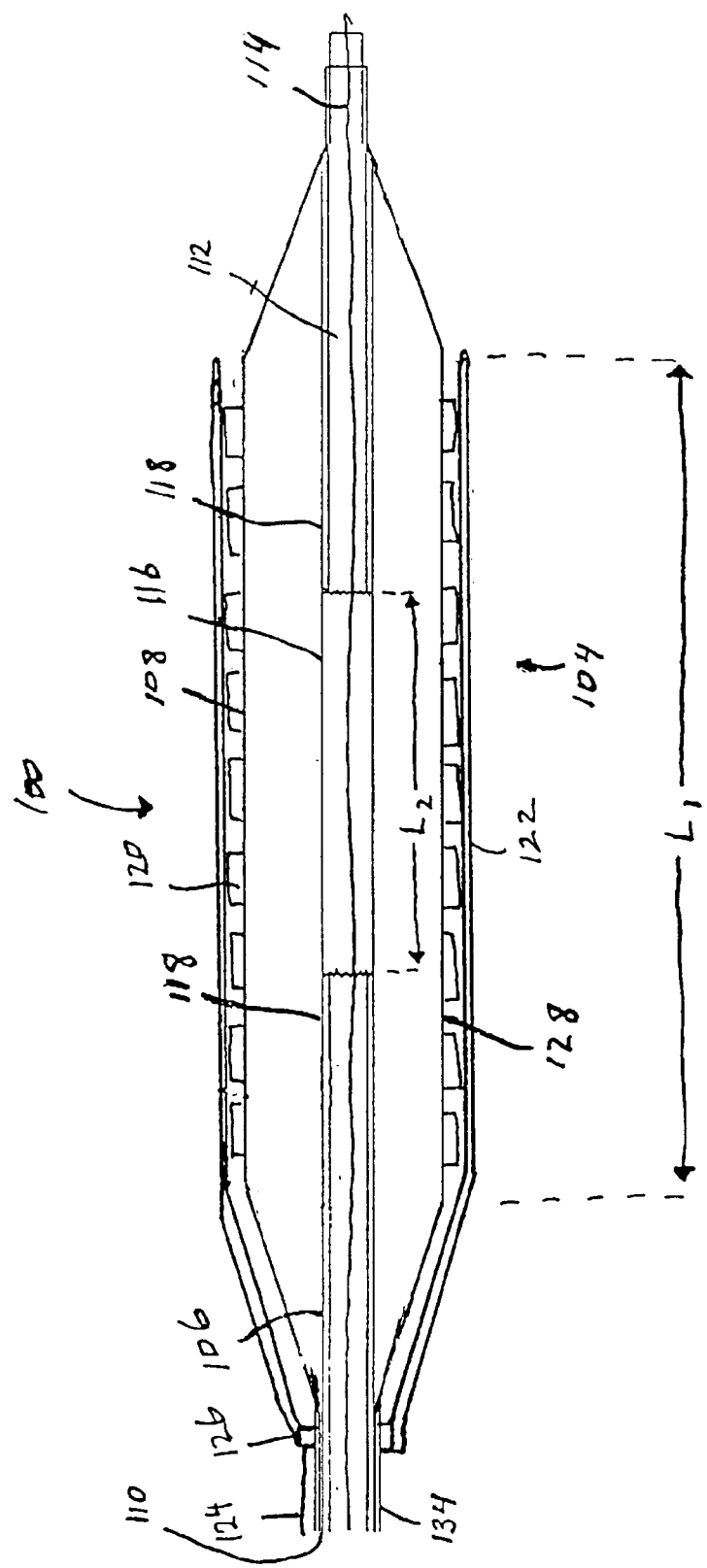
FIG. 7 shows an inventive balloon catheter similar to that of FIG. 1 with a prosthesis disposed about the medical balloon.

The inventive balloon catheter may also be provided for the purposes of delivering an expandable prosthesis to a desired bodily location. Suitable prostheses include stents, stent-grafts and grafts. As shown in FIG. 7, stent 120 is disposed about medical balloon 108. Catheter 100 further comprises retractable sheath 122 disposed about stent 120. Retractable sheath 122 may be retracted in a proximal direction by pulling on pull wire 124 which extends proximally from sheath 122. Pull wire 124 is attached to retractable sheath 122 via pull collar 126. Any other suitable retraction mechanism as known in the art may also be used.

Figure 8:
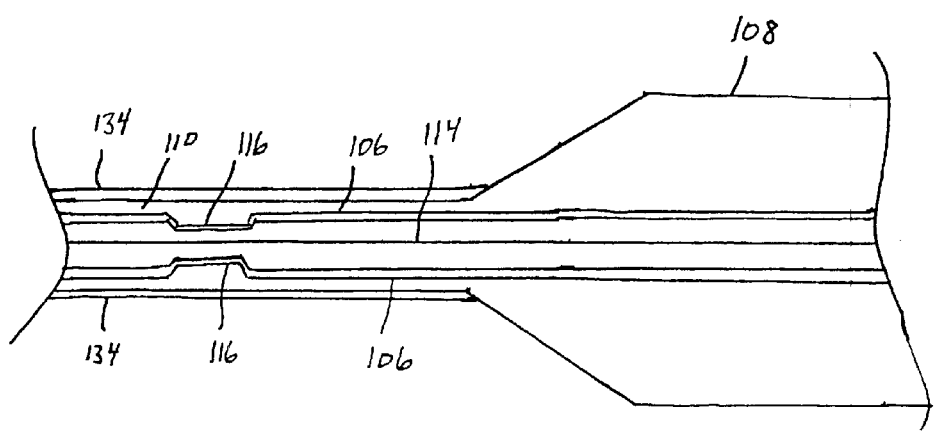
FIG. 8 is a side view of an inventive balloon catheter with parts cut away at the distal end, the inner tube including a collapsible portion located proximal of the medical balloon.

In the embodiments of FIGS. 1–7, the medical balloon is disposed about the collapsible portion of the inner tube. The invention also is directed to embodiments in which the collapsible portion of the inner tube is displaced along the catheter relative to the medical balloon. In one such embodiment, as shown in FIG. 8, collapsible portion 116 is located proximal of medical balloon 108. The collapsible portion may also be located distal of the medical balloon.

In all of the above embodiments, the catheter is desirably constructed so that the collapsible portion is substantially restored to its original configuration upon withdrawal of the inflation fluid from the medical balloon thereby releasing the inner tube from the guidewire.

The inventive balloon catheter may be provided in a number of different configurations including in an over-the-wire configuration and in a rapid exchange configuration. In the former configuration, the guidewire is carried internally along the entire length of the catheter. In the latter configuration, as shown in FIG. 9, guidewire 114 exits catheter 100 through guidewire port 132 at a position distal to the proximal end of the catheter. Guidewire 114 extends in inner tube 106. Inner tube 106 extends in outer tube 134. The catheter may also be provided in a convertible configuration, usable in either an over the wire configuration or in a rapid exchange configuration. Additional information concerning these configurations may be found in U.S. Pat. No. 6,120,522.

In the above embodiments, the inflation lumen for the medical balloon is provided in the space between the outer tube and the inner tube. It is also within the scope of the invention for the inflation lumen to provided in other suitable arrangements so long as the inflation fluid which is delivered to the medical balloon can apply an inward force to the collapsible portion(s) of the inner tube.

In another embodiment, the invention is directed to a method of securing a catheter inner tube to a guidewire disposed in the inner tube. In accordance with the inventive method, a catheter such as one of those described above is provided and an inflation fluid delivered to the medical balloon to cause the collapsible portion of the inner tube to collapse inward against the guidewire and secure the inner tube to the guidewire. The inner tube may optionally be released from the guidewire by withdrawing the inflation fluid from the medical balloon.

In another embodiment, the invention is directed to a method of dilating a vessel. The method comprises the steps of providing a catheter such as one of those disclosed above, inserting the catheter in a body and delivering the medical balloon portion of the catheter to a desired location in a bodily vessel. The medical balloon is inflated to a pressure sufficient to apply a force to the vessel by supplying an inflation fluid to the medical balloon. The supplying of inflation fluid causes the collapsible portion of the inner tube to collapse inward against the guidewire and secure the inner tube to the guidewire. The inner tube may optionally be released from the guidewire by withdrawing the inflation fluid from the medical balloon.

The invention is also directed to a method of delivering a prosthesis to a desired location in a bodily vessel. The method comprises the steps of providing any of the catheters disclosed above with a prosthesis disposed about the medical balloon, inserting the catheter in a body and delivering the medical balloon to a desired location in a bodily vessel. The medical balloon is inflated to a pressure sufficient to expand the prosthesis and implant the prosthesis in the vessel by supplying an inflation fluid to the medical balloon. The supplying of the inflation fluid causes the collapsible portion of the inner tube to collapse inward against the guidewire and secure the inner tube to the guidewire. The method may further comprise the steps of withdrawing the inflation fluid from the medical balloon to release the inner tube from the guidewire and withdrawing the catheter from the body. Any of the above-disclosed prostheses may be used. Desirably, the prosthesis is a stent.

The above disclosure is intended to be illustrative and not exhaustive. This description will suggest many variations and alternatives to one of ordinary skill in this art. All these alternatives and variations are intended to be included within the scope of the claims where the term "comprising" means "including, but not limited to". Those familiar with the art may recognize other equivalents to the specific embodiments described herein which equivalents are also intended to be encompassed by the claims.

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below (e.g. claim 3 may be taken as alternatively dependent from claim 2; claim 5 may be taken as alternatively dependent on claim 1, 2 or 3; etc.).

This completes the description of the preferred and alternate embodiments of the invention. Those skilled in the art may recognize other equivalents to the specific embodiment described herein which equivalents are intended to be encompassed by the claims attached hereto.

What is claimed is:

1. A balloon catheter comprising an inner tube with a guidewire lumen therein, a medical balloon and an inflation lumen, the inner tube having a guidewire lumen, a guidewire being within the guidewire lumen and being isolated from the inflation lumen over the entire length of the guidewire, the medical balloon disposed about the inner tube and in fluid communication with the inflation lumen, wherein a collapsible portion of the inner tube is constructed to collapse inward upon delivery of an inflation fluid to the medical balloon and grip the guidewire and to release from the guidewire upon removal of the inflation fluid.

2. The balloon catheter of claim 1 wherein the collapsible portion of the inner tube is a distal portion of the inner tube.

3. The balloon catheter of claim 1 wherein the collapsible portion of the inner tube is made of an elastomeric material.

4. The balloon catheter of claim 3 wherein portions of the inner tube adjacent the elastomeric material are made of a non-elastomeric material.

5. The balloon catheter of claim 4 further comprising a prosthesis disposed about the medical balloon.

6. The balloon catheter of claim 5 wherein the prosthesis is a stent.

7. The balloon catheter of claim 4 wherein the collapsible portion of the inner tube grips the guidewire when the balloon is partially inflated.

8. The balloon catheter of claim 5 wherein the collapsible portion of the inner tube grips the guidewire when the balloon is partially inflated.

9. The balloon catheter of claim 1 wherein the collapsible portion is at least 2 mm long.

10. The balloon catheter of claim 1 in a rapid exchange configuration.

11. The balloon catheter of claim 1 wherein the collapsible portion of the inner tube recoils upon removal of the inflation fluid.

12. A balloon catheter comprising an inner tube with a guidewire lumen therein capable of housing a guidewire, a medical balloon and an inflation lumen, the inflation lumen isolated from the guidewire lumen, the guidewire lumen extending proximally from a distal portion of the catheter to a port constructed and arranged to provide entry of a guidewire into the catheter, the medical balloon disposed about the inner tube and in fluid communication with the inflation lumen, wherein the inner tube includes a first portion and a second portion adjacent to the first portion, the second portion is weaker than the first portion, the second portion deforming inward upon delivery of an inflation fluid to the medical balloon.

13. The balloon catheter of claim 12 wherein the inner tube is constructed and arranged such that the second portion recoils upon the removal of inflation fluid from the balloon.

14. A balloon catheter comprising an inner tube with a guidewire therein, a medical balloon and an inflation lumen, the inflation lumen designed to contain an inflation fluid and outside of the inner tube, the inner tube separating the inflation fluid within the catheter from the entire length of the guidewire within the catheter, the medical balloon disposed about the inner tube and in fluid communication with the inflation lumen, wherein a collapsible portion of the inner tube is constructed to collapse inward upon pressurizing the balloon to grip the guidewire and to release the guidewire upon depressurizing the balloon.

* * * * *